United States Patent
Licato et al.

(10) Patent No.: US 6,356,780 B1
(45) Date of Patent: Mar. 12, 2002

(54) METHOD AND APPARATUS FOR MANAGING PERIPHERAL DEVICES IN A MEDICAL IMAGING SYSTEM

(75) Inventors: Paul E. Licato, Wauwatosa; Peter C. Bosch, Waukesha; Suriyanarayana Venkatraman, Milwaukee; Robert Steven Stormont, Hartland, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/469,999

(22) Filed: Dec. 22, 1999

(51) Int. Cl.[7] .................................................. A61B 5/05
(52) U.S. Cl. ........................ 600/407; 600/409; 600/410; 600/425; 600/427; 600/473; 600/476; 382/128; 705/2; 705/3
(58) Field of Search .............................. 600/407, 409, 600/410, 413, 415, 417, 422, 425, 427, 430, 437, 438, 473, 474, 476, 300, 310, 372, 373; 324/260, 307, 318, 321, 322; 378/21, 4, 62, 70, 91; 382/128, 320, 321; 705/2, 3

(56) References Cited

U.S. PATENT DOCUMENTS

| | | | | |
|---|---|---|---|---|
| 4,712,560 A | * | 12/1987 | Schaefer et al. .......... 128/653.2 |
| 5,243,655 A | * | 9/1993 | Wang .......................... 380/51 |
| 5,311,135 A | * | 5/1994 | Vavrek et al. .............. 324/318 |
| 5,551,430 A | | 9/1996 | Blakeley et al. .......... 128/653.2 |
| 5,781,442 A | * | 7/1998 | Engleson et al. ....... 364/478.02 |
| 5,782,805 A | * | 7/1998 | Meinzer et al. ............. 604/131 |
| 5,853,005 A | * | 12/1998 | Scanlon ........................ 5/83.1 |
| 6,092,722 A | * | 7/2000 | Heinrichs et al. ........... 235/375 |
| 6,206,829 B1 | * | 3/2001 | Iliff ............................. 600/300 |

* cited by examiner

Primary Examiner—Marvin M. Lateef
Assistant Examiner—Jeoyuh Lin
(74) Attorney, Agent, or Firm—Fletcher, Yoder & Van Someren

(57) ABSTRACT

A technique for managing data relating to peripheral devices and subsystems in an imaging system includes providing memory circuitry and, where desired, signal processing circuitry resident in the peripheral devices. Manufacturing data, identification data, service record information, calibration data, and other relevant information may be stored directly in the peripheral devices. The circuitry of the peripherals and subsystems may also include sensors and encryption circuits, and circuits for interfacing the memory and processing circuitry with other components, particularly a controller for an imaging system. The peripherals may include coils and drivers for MRI systems, tables, patient monitors and any other device pertinent to an MRI system. An initialization sequence is performed upon connection of the peripheral to the system, to identify the peripheral and to transfer information needed for examination sequences and other MRI procedures.

48 Claims, 4 Drawing Sheets

METHOD AND APPARATUS FOR MANAGING PERIPHERAL DEVICES IN A MEDICAL IMAGING SYSTEM

FIELD OF THE INVENTION

The present invention relates generally to the field of imaging systems including one or more peripheral devices, such as systems used in the medical diagnostics field. More particularly, the invention relates to a technique for managing peripheral devices in an imaging system in which certain information and functionalities are stored within circuitry of the peripheral device itself and retrieved as needed by the system.

BACKGROUND OF THE INVENTION

A wide variety of imaging systems have been developed and are presently in use, particularly in the medical diagnostics field. While very simple imaging systems may comprise self-contained image acquisition and processing components and circuitry, more complex systems include various peripheral devices which may be associated with other system components as needed. In the medical imaging field, for example, systems are typically considered by imaging modality. These modalities may include magnetic resonance imaging (MRI) systems, computed tomography (CT) systems, ultrasound systems, x-ray systems, positron emission tomography (PET) systems, and so forth. Depending upon the physics involved in acquiring and reconstructing useful images, these systems call upon different control and processing circuitry, as well as peripheral devices for data acquisition, processing, storage, and output or viewing.

By way of example, in an MRI system, image data is acquired by imposing magnetic fields on a subject, including a primary magnetic field and a series of gradient fields. The fields define an imaging slice through the subject and encode positions of materials of interest in the selected slice as a function of frequency. After imposition of radio frequency pulses, transverse moments are produced in gyromagnetic material of the subject through the slice, and echo signals from the material can be sensed and processed to identify the intensity of the response at the various locations in the slice. After data processing, an image can be reconstructed based upon the acquired and processed data.

Continuing with the example of an MRI system, various peripheral devices are typically used in the image acquisition, processing, reconstruction, and output of useful images. Depending upon the system design, various types and configurations of RF coils are used to excite the gyromagnetic material, and to capture response signals. In a broad sense, subsystems of the overall imaging system may be considered peripherals, including gradient coils, a primary magnet, a table or support on which a patient is positioned, and so forth. Each of these peripheral devices or subsystems must be properly controlled to reliably produce the desired image data. Similar peripheral devices and subsystems are present in the other modality imaging equipment, particularly in x-ray systems, CT systems, ultrasound systems, and so forth.

Proper coordination of subsystems and peripheral devices in imaging systems is critical to the capture, processing and display of desired images. In particular, many subsystems and peripheral devices must be appropriately calibrated to account for device-to-device variances and tolerances, as well as for similar tolerances within individual devices. Moreover, where alternative devices are employed in a system, such as RF coils in an MRI system, the devices typically have different characteristics which must be taken into account during both the image data acquisition operation and during subsequent data processing.

At present, peripheral devices in medical diagnostic equipment are identified and selected by clinicians and radiologists, and typically identified to the imaging system via an operator input. In the specific example described above, an RF coil in an MRI system would be selected depending upon the anatomy to be imaged and the available imaging protocols of an individual system, and the operator would then identify the coil to the controller. The controller, or memory associated with the controller, may then call upon stored data representative of known or calibrated characteristics of the coil. If the operator improperly identifies the coil, or if the characteristics of the coil are erroneously referenced, appropriate image data will not be collected, or time is lost in identifying or correcting the identification and peripheral data problem.

In addition to the identification and calibration data for imaging system peripherals, various information is typically known relating to manufacturing, servicing, and other historical details of the subsystems and peripherals. This information may be extremely useful in evaluating performance of various peripheral devices, anticipating potential maintenance issues, and correcting or tracing manufacturing or servicing records. At present, this information is generally stored in cross-referenced files of imaging system control circuitry, or, more commonly, in entirely separate manufacturing and service records at diverse locations, including at a hospital or medical institution, at individual service providers, and so forth.

There is a need for an improved technique for managing data relating to imaging system peripherals and subsystems. There is a particular need at present for a technique which may be applied to a wide variety of peripheral devices, permitting more efficient identification of the devices themselves, as well as calibration, service history, and other data which may be of use in the imaging process or in the servicing and maintenance of the system.

SUMMARY OF THE INVENTION

The invention provides a technique for managing imaging system peripheral data designed to respond to these needs. The technique may be applied to a wide range of practical applications, but is particularly well suited to complex imaging systems used in the medical diagnostics field. Within that field, the technique has particular promise for managing data in MRI systems, CT systems, x-ray systems, PET systems, and so forth. In a general sense, the technique permits data to be stored within the peripheral device or subsystem itself. This data may include a minimal data set, such as the identity of the peripheral device, or more elaborate data sets, such as calibration information, service history, manufacturing history, usage information, and the like. Moreover, functional data, including programs and subroutines, may be stored within the peripheral device and made executable upon demand. Finally, the circuitry permitting the storage and access to the peripheral device data may include circuitry for encrypting and decrypting information, or for providing limited access to the data, such as by authorized service personnel.

In accordance with one aspect of the technique, memory and communications circuitry is included as an integral part of the peripheral device. Identification data is stored in the device for subsequent access by an imaging system. Upon connection of the peripheral device to the imaging system, the data may be retrieved and an imaging sequence performed based upon the retrieved information. The retrieved information may be cross-referenced to data, such as calibration data or service history data in a memory circuit external to the periphery device. However, where desired, this information may be stored directly in the circuitry of the peripheral device for direct access, loading and use by the external components. Because the information remains resident in the peripheral device, it can be freely accessed, uploaded, downloaded, modified and used whether the peripheral device is employed with the imaging system or apart from the imaging system, such as in a remote servicing location.

DETAILED DESCRIPTION OF THE INVENTION

Figure 1:
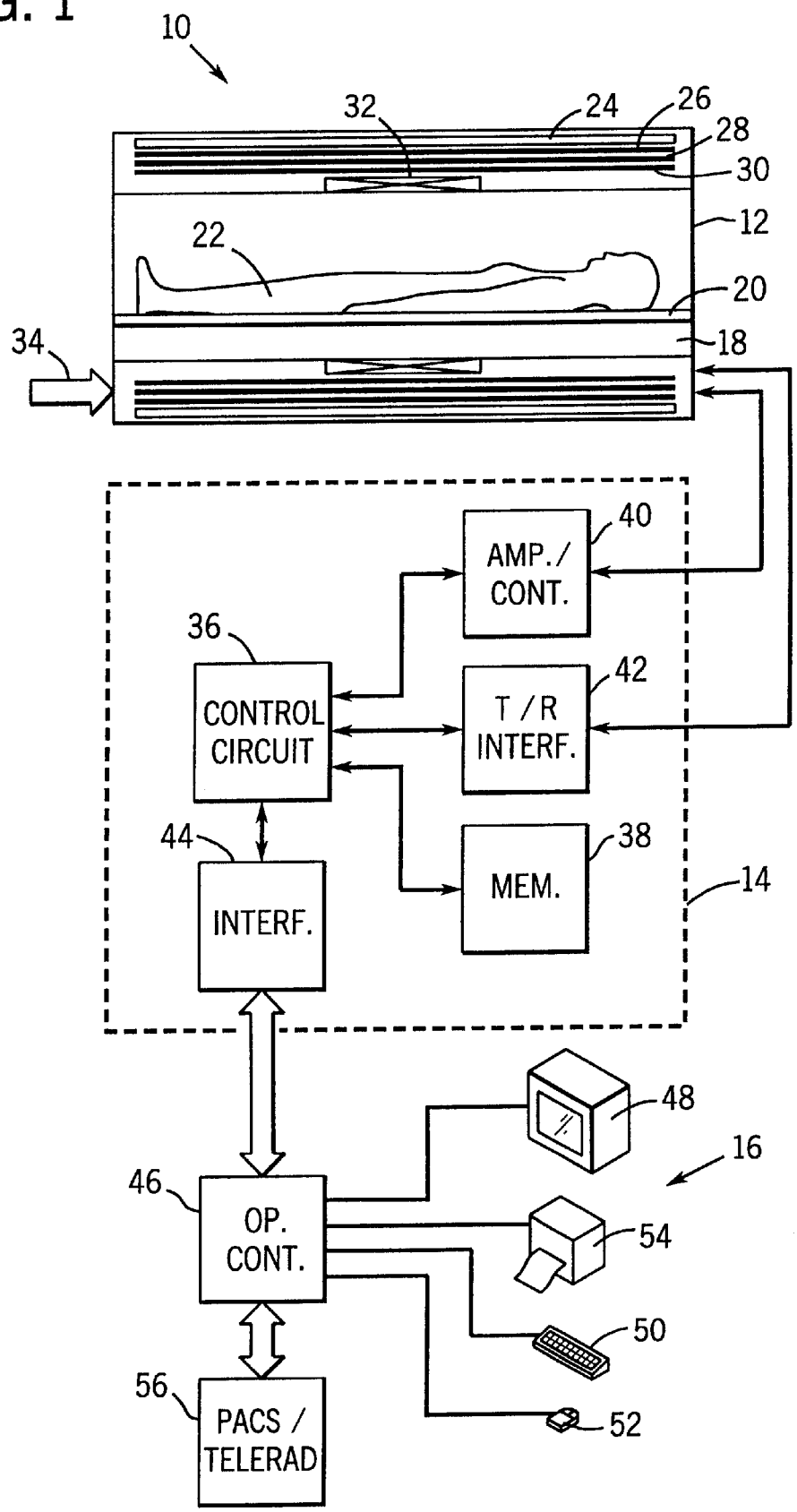
FIG. 1 is a diagrammatical representation of an exemplary imaging system in the form of an MRI system, including peripheral devices and subsystems capable of storing and retrieving data in accordance with aspects of the present technique.

Turning now to the drawings, and referring to FIG. 1, an exemplary imaging system, in the form of a magnetic resonance imaging (MRI) system 10 is illustrated diagrammatically as including a data acquisition system 12, a control system 14, and an interface system 16. Some or all of these systems include components which may store and access data for use in imagine or servicing as described more fully below. While system 10 may include any suitable scanner or detector, in the illustrated embodiment the system includes a full body scanner comprising a patient bore 18, into which a t able 20 may be positioned to place a patient 22 in a desired orientation for scanning. Data acquisition system 12 may be of any suitable rating, including ratings varying from 0.2 Tesla to 1.5 Tesla, and beyond.

Data acquisition system 12 includes a series of associated coils for producing controlled magnetic fields, and for generating radio frequency excitation pulses, and for detecting emissions from gyromagnetic material within the patient in response to such pulses. In the diagrammatical view of FIG. 1, a primary magnet 24 is provided for generating a primary magnetic field, generally aligned with the patient bore. A series of gradient coils 26, 28 and 30 are group ed in a coil assembly for generating controlled magnetic gradient fields during examination sequences. A radio frequency coil 32 is provided for generating radio frequency pulses for exciting the gyromagnetic material. In the embodiment illustrated in FIG. 1, coil 32 also serves as a receiving coil. Thus, RF coil 32 may be coupled with driving and receiving circuitry in passive and active modes for receiving emissions from gyromagnetic material and for outputting radio frequency excitation pulses, respectively. Alternatively, various configurations of receiving coils may be provided separate from RF coil 32. Such coils may include structures specifically adapted for target anatomies, such as head coil assemblies, and so forth. Moreover, receiving coils may be provided in any suitable physical configuration, including phased array coils, and so forth.

As will be appreciated by those skilled in the art, in the case of the MRI system illustrated, when gyromagnetic material, typically bound in tissues of the patient, is subjected to the primary field, individual magnetic moments of the paramagnetic nuclei in the tissue attempt to align with the field but precess in a random order at their characteristic or Larmor frequency. While a net magnetic moment is produced in the direction of the polarizing field, the randomly oriented components of the moment in a perpendicular plane generally cancel one another. During an examination sequence, an RF excitation pulse is generated at or near the Larmor frequency of the material of interest, resulting in rotation of the net aligned moment to produce a net transverse magnetic moment. Radio signals are emitted following termination of the excitation signals. This magnetic resonance signal is detected in the scanner and processed for reconstruction of the desired image.

As a basis for the present discussion of peripheral devices and subsystems equipped to store, access and manage data, a brief description of the operation of an MRI system is provided below. It should be borne in mind, however, that while the present technique is particularly well suited to MRI and similar medical diagnostic systems, it is not intended to be limited to any particular type, design, or modality system.

In the MRI system of FIG. 1, gradient coils 26, 28 and 30 serve to generate precisely controlled magnetic fields, the strength of which vary over a predefined field of view, typically with positive and negative polarity. When each coil is energized with known electric current, the resulting magnetic field gradient is superimposed over the primary field and produces a linear variation in the overall magnetic field strength across the field of view. Combinations of such fields, orthogonally disposed with respect to one another, enable the creation of a linear gradient in any direction by vector addition of the individual gradient fields.

The gradient fields may be considered to be oriented both in physical planes, as well as by logical axes. In the physical sense, the fields are mutually orthagonally oriented to form a coordinate system which can be rotated by appropriate manipulation of the pulsed current applied to the individual field coils. In a logical sense, the coordinate system defines gradients which are typically referred to as slice select gradients, frequency encoding gradients, and phase encoding gradients.

The slice select gradient determines a slab of tissue or anatomy to be imaged in the patient. The slice select gradient field may thus be applied simultaneous with a selective RF pulse to excite a known volume of spins within a desired slice that precess at the same frequency. The slice thickness is determined by the bandwidth of the RF pulse and the gradient strength across the field of view.

A second logical gradient axis, the frequency encoding gradient axis is also known as the readout gradient axis, and is applied in a direction perpendicular to the slice select gradient. In general, the frequency encoding gradient is applied before and during the formation of the MR echo signal resulting from the RF excitation. Spins of the gyromagnetic material under the influence of this gradient are frequency encoded according to their spatial position across the gradient field. By Fourier transformation, acquired signals may be analyzed to identify their location in the selected slice by virtue of the frequency encoding.

Finally, the phase encode gradient is generally applied in a sequence before the readout gradient and after the slice select gradient. Localization of spins in the gyromagnetic material in the phase encode direction is accomplished by sequentially inducing variations in phase of the precessing protons of the material by using slightly different gradient amplitudes that are sequentially applied during the data acquisition sequence. Phase variations are thus linearly imposed across the field of view, and spatial position within the slice is encoded by the polarity and the degree of phase difference accumulated relative to a null position. The phase encode gradient permits phase differences to be created among the spins of the material in accordance with their position in the phase encode direction.

As will be appreciated by those skilled in the art, a great number of variations may be devised for pulse sequences employing the logical axes described above. Moreover, adaptations in the pulse sequences may be made to appropriately orient both the selected slice and the frequency and phase encoding to excite the desired material and to acquire resulting MR signals for processing.

The coils of system 12 are controlled by control system 14 to generate the desired magnetic field and radio frequency pulses. In the diagrammatical view of FIG. 1, control system 14 thus includes a control circuit 36 for commanding the pulse sequences employed during the examinations, and for processing received signals. Control circuit 36 may include any suitable programmable logic device, such as a CPU or digital signal processor of a general purpose or application-specific computer. Control circuit 36 further includes memory circuitry 38, such as volatile and non-volatile memory devices for storing physical and logical axis configuration parameters, examination pulse sequence descriptions, acquired image data, programming routines, and so forth, used during the examination sequences implemented by the scanner.

Interface between the control circuit 36 and the gradient coils of data acquisition system 12 is managed by amplification and driver circuitry 40. RF coil 32 is similarly interfaced by transmission and receive interface circuitry 42. Circuitry 40 includes amplifiers for each gradient field coil to supply drive current to the field coils in response to control signals from control circuit 36. Interface circuitry 42 includes additional power amplification circuitry for driving RF coil 32. Moreover, where the RF coil serves both to emit the radio frequency excitation pulses and to receive MR signals, circuitry 42 will typically include a switching device for toggling the RF coil between active or transmitting mode, and passive or receiving mode. A power supply, denoted generally by reference numeral 34 in FIG. 1, is provided for energizing the primary magnet 24. Finally, circuitry 14 includes interface components 44 for exchanging configuration and image data with interface system 16.

Interface system 16 may include a wide range of devices for facilitating interface between an operator or radiologist and data acquisition system 12 via control system 14. In the illustrated embodiment, for example, an operator controller 46 is provided in the form of a computer work station employing a general purpose or application-specific computer. The station also typically includes memory circuitry for storing examination pulse sequence descriptions, examination protocols, user and patient data, image data, both raw and processed, and so forth. The station may further include various interface and peripheral drivers for receiving and exchanging data with local and remote devices. In the illustrated embodiment, such devices include a conventional computer keyboard 50 and an alternative input device such as a mouse 52. A printer 54 is provided for generating hard copy output of documents and images reconstructed from the acquired data. A computer monitor 48 is provided for facilitating operator interface. In addition, system 10 may include various local and remote image access and examination control devices, represented generally by reference numeral 56 in FIG. 1. Such devices may include picture archiving and communication systems, teleradiology systems, and the like.

Figure 2:
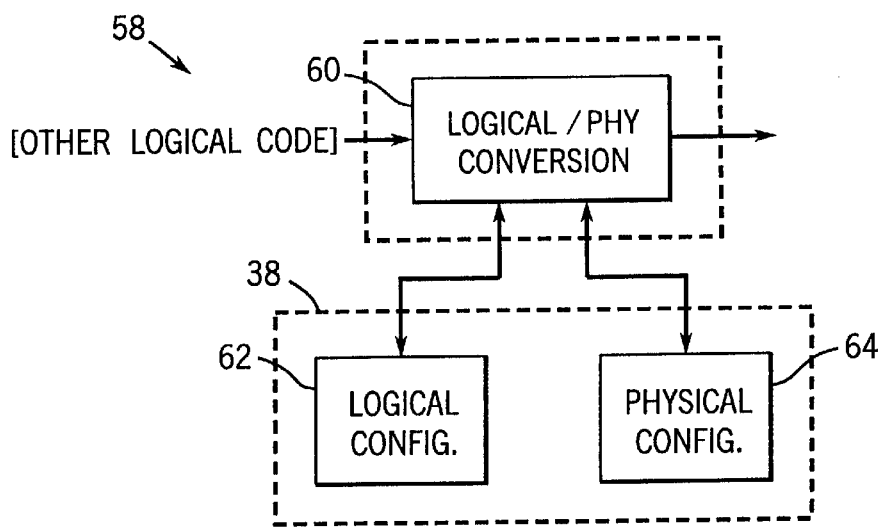
FIG. 2 is a diagrammatical representation of certain of the logical circuitry of the system of FIG. 1.

Depending upon the physics (i.e. the modality) of the imaging system 10, examinations will be performed to produce image data for reconstruction of a useful image. In the case of an MRI system, for example, these examinations include pulse sequences carried out by application of control signals to the gradient and RF coils, and by receiving resulting signals from the subject. In general, these pulse sequences will be defined by both logical and physical configuration sets and parameter settings stored within control system 14. FIG. 2 represents, diagrammatically, relationships between functional components of control circuit 36 and configuration components stored with memory circuitry 38. The functional components facilitate coordination of the pulse sequences to accommodate preestablished settings for both logical and physical axes of the system. In general, the axis control modules, denoted collectively by reference numeral 58, include a logical-to-physical module 60 which is typically implemented via software routines executed by control circuit 36. In particular, the conversion module is implemented through control routines which define particular pulse sequences in accordance with preestablished imaging protocols.

When called upon, code defining the conversion module references logical configuration sets 62 and physical configuration sets 64. The logical configuration sets may include parameters such as pulse amplitudes, beginning times, time delays, and so forth, for the various logical axes described above. The physical configuration sets, on the other hand, will typically include parameters related to the physical constraints of the scanner itself, including maximum and minimum allowable currents, switching times, amplification, scaling, and so forth. Conversion module 60 serves to generate the pulse sequence for driving the coils of scanner 12 in accordance with constraints defined in these configuration sets. The conversion module will also serve to define adapted pulses for each physical axis to properly orient (e.g. rotate) slices and to encode gyromagnetic material in accordance with desired rotation or reorientations of the physical axes of the image.

Figure 3:
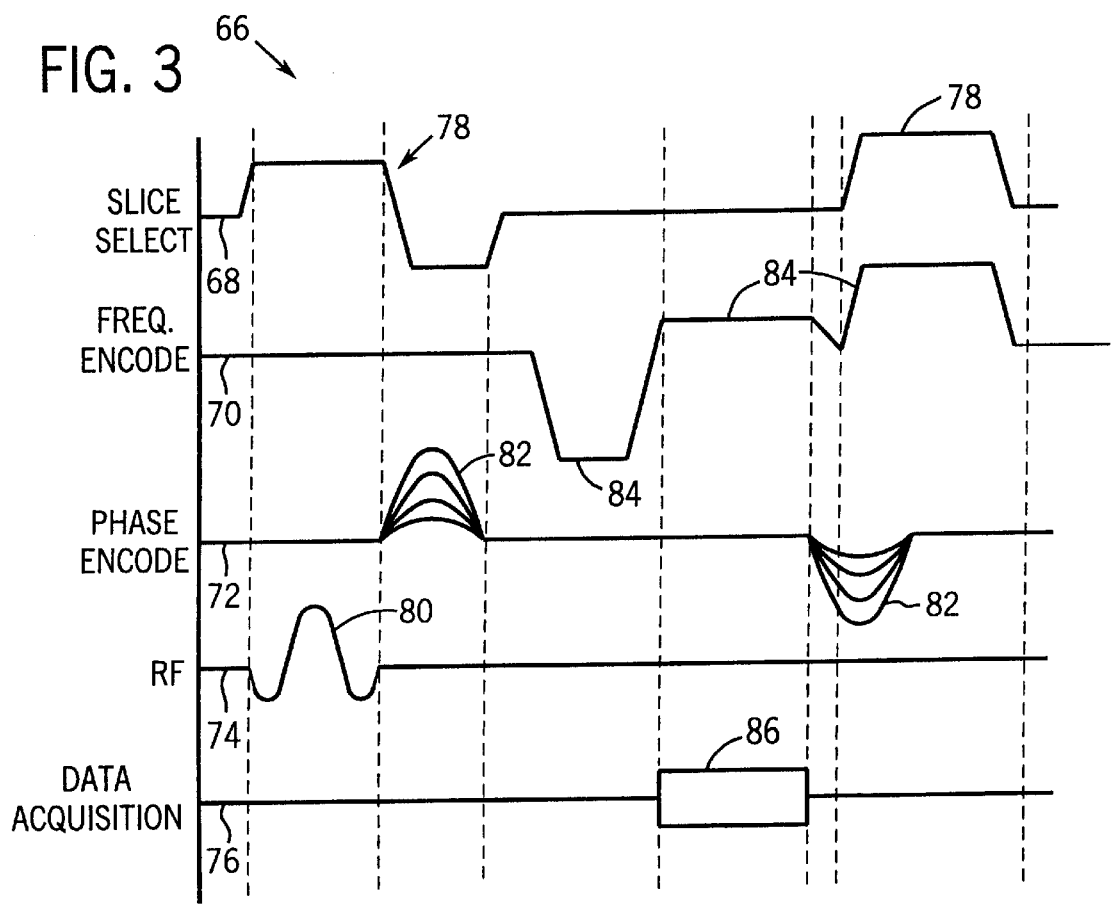
FIG. 3 is a graphical representation of an exemplary examination sequence which may be carried out in an imaging system such as that illustrated in FIG. 1.

By way of example, FIG. 3 illustrates a typical pulse sequence which may be implemented on a system such as that illustrated in FIG. 1 and calling upon configuration and conversion components such as those shown in FIG. 2. While many different pulse sequence definitions may be implemented, depending upon the examination type, in the example of FIG. 3, a gradient recalled acquisition in steady state mode (GRASS) pulse sequence is defined by a series of pulses and gradients appropriately timed with respect to one another. The pulse sequence, indicated generally by reference numeral 66, is thus defined by pulses on a logical slice select axis 68, a frequency encoding axis 70, a phase encoding axis 72, an RF axis 74, and a data acquisition axis 76. In general, the pulse sequence description begins with a pair of gradient pulses on slice select axis 68 as represented at reference numeral 78. During a first of these gradient pulses, an RF pulse 80 is generated to excite gyromagnetic material in the subject. Phase encoding pulses 82 are then generated, followed by a frequency encoding gradient 84. A data acquisition window 86 provides for sensing signals resulting from the excitation pulses which are phase and frequency encoded. The pulse sequence description terminates with additional gradient pulses on the slice select, frequency encoding, and phase encoding axes.

As will be appreciated by those skilled in the art, the foregoing operation of an MRI system, and other procedures for obtaining image data on other modality imaging systems calls for a number of peripheral devices and subsystems operating in concert. For example, in the foregoing example, the pulse sequence description is typically stored within the control system 14, and carried out upon request. However, various pulse sequences may call for different peripheral devices, such as RF coils 32. In a typical application, a clinician or radiologist will select an examination via interface system 16, and insert the appropriate RF coil in the data acquisition system 12. Similarly, the table on which the patient is positioned will be placed in the appropriate orientation, and the gradient coils will be prepared for the examination sequence. Well before these procedures are carried out, calibration procedures are performed on all of these peripheral devices, as well as on other components of the system. When the operator selects the examination sequence, an identification of the peripheral devices associated with the system, such as RF coil 32, is input through the interface system 16. The calibration information for the coil, as well as other relevant information is, in these prior art techniques, accessed from a storage device, typically the memory circuitry 38 of the imaging system itself.

Figure 4:
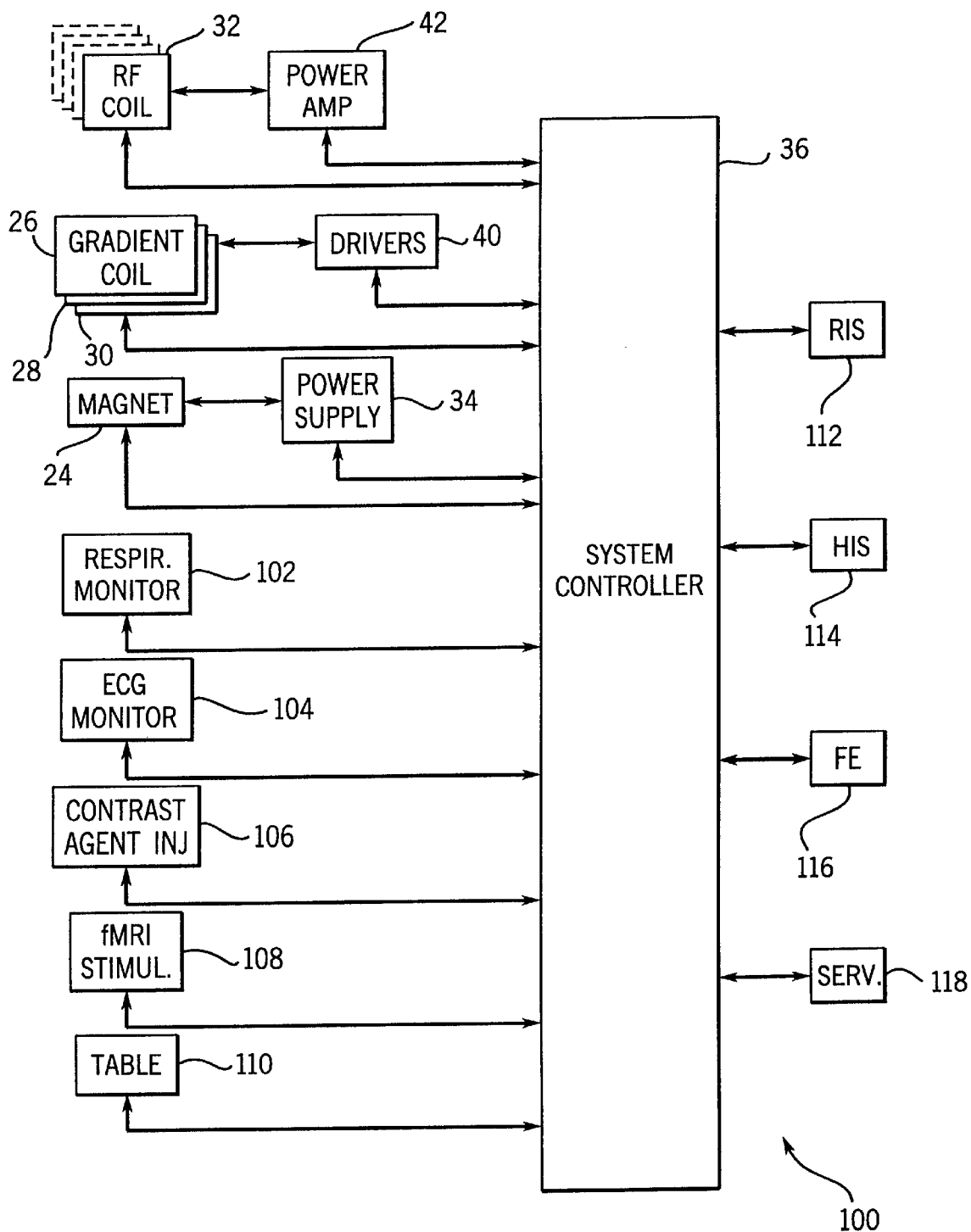
FIG. 4 is a diagrammatical representation of an exemplary peripheral topology in which data is stored within and accessed from various subsystems and peripheral devices.

The present technique permits such information to be stored in each peripheral device or subsystem. FIG. 4 illustrates an exemplary peripheral topology 100 available through the present technique. As illustrated diagrammatically in FIG. 4, a wide variety of the peripherals and subsystems of the imaging system may include circuitry for storing and accessing identification data, calibration data, and other useful information and functional code. In the embodiment illustrated in FIG. 4, each of these devices, illustrated on the left of system controller 36, can receive and transmit data in digital form through system controller 36 for use in examination sequences and servicing. These peripherals and subsystems include the RF coils 32 and power amplification circuitry 42 for driving the coils. Each individual coil may include circuitry for storage of the data, as may the power amplification circuitry. Other such peripheral devices and subsystems may include gradient coils 26, 28 and 30, as well as driver circuitry 40 for controlling the fields produced by the gradient coils. Magnet 24, as well as its power supply 34, may be similarly equipped. In MRI systems, as well as in other medical diagnostic imaging equipment, similar peripheral devices may further include respiration monitors 102, ECG monitors 104, and contrast agent injection devices 106. In the case of MRI systems, stimulating devices for functional MRI (FMRI) examinations may be equipped for storing and accessing data, as indicated at reference numeral 108. Finally, additional components of the system, such as table 20 may be equipped with circuitry, as indicated at reference numeral 110 in FIG. 4, for providing similar information.

The information which may be stored and accessed in the various peripheral devices may vary widely depending upon the nature of the peripheral device and its use in the system. For example, in the case of gradient coils and RF coils of an MRI system, data may be stored in each device to provide an indication of the peripheral type, its identification, the manufacturing date and source, and field strength. Calibration information resulting from separate calibration sequences may also be stored in the devices. Finally, service histories, including references or code indicative of particular services performed on the devices or problems encountered in the devices in the past may be similarly stored directly on the device. Other devices may have unique information associated with them which may be similarly stored. For example, the circuitry 110 associated with the table for positioning a patient in an MRI system may include data indicative of weight limitations of the table which are accessed and used by the system during examinations. The information may serve as a basis, for example, in notifications or alarms output to clinicians when weight limits are approached or exceeded.

In addition to storing and accessing informational data, each peripheral device or subsystem may further include executable code which may be carried out in coordination with system controller 36, or other external circuitry. For example, calibration algorithms, autocalibration procedures, and so forth, may be stored in peripheral devices requiring such calibration for examination sequences. These programs may be self executing upon connection of the devices to the system, as described below, or may be accessed and executed upon an operator prompt or upon a call sequence from a routine executed by the external components.

The peripheral devices and subsystems illustrated in FIG. 4, as well as other peripheral devices which may be added or useful in the system, preferably communicate through system controller 36. As noted above, system controller may store information on each device, and access the information as desired for particular imaging needs. Moreover, system controller 36 may act as an interface for conveying certain of the information to other systems, both within an institution and outside the institution. As illustrated in FIG. 4, for example, a radiology department informational system 112 may be coupled to system controller, such as via an intranet or the like, to access information from the peripheral devices and subsystems, and to download information to each device as desired. Similar information exchange may be performed with a hospital information system, as indicated at reference numeral 114. A field engineer station 116 may similarly communicate with the peripheral devices and subsystems through system controller 36. For example, a field engineer laptop may be coupled to a system controller for accessing service records, calibration information, usage information, and so forth, from each device. Finally, in the embodiment illustrated in FIG. 4, a remote servicing facility 118 may communicate with system controller to access the data from the peripheral devices and subsystems. The service facility accessing in this manner may be entirely remote from the imaging system or institution, such as in a remote service center connected to the institution via an open wide area network, such as the Internet, a virtual proprietary network or the like.

Figure 5:
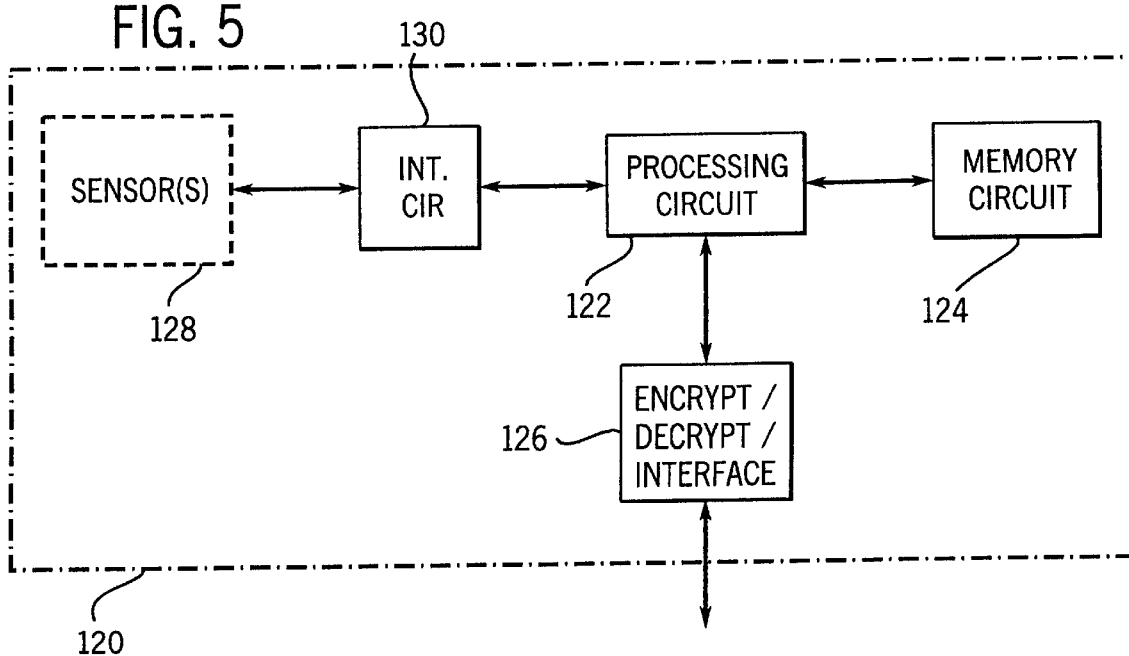
FIG. 5 is a diagrammatical representation of the topology of various functional circuitry within a peripheral device equipped to store and access data.

Various configurations for the storage of data and code may be envisaged, which may be incorporated directly into the imaging system peripheral devices and subsystems. FIG. 5 illustrates an exemplary peripheral topology 120 in accordance with a present embodiment. In this topology, a processing circuit 122 is provided for executing any functional code, exchanging data, responding to data requests, and so forth. Processing circuit 122, which may typically include a programmed microprocessor, draws data from a memory circuit 124 where the data is stored. The memory circuit may include any suitable type of memory, but preferably includes non-volatile memory capable of retaining the data when power is removed from the peripheral device or subsystem. Processing circuit 122 may also write data to the memory circuit, such as upon initial manufacturing and testing of the device, following calibration sequences, following service events, and so forth. Where the peripheral device or subsystem includes sensors 128, these also form part of the preferred topology. Such sensors may be provided, for example, for detecting temperatures of coils, acoustical signals for cardiac monitors, flow rates for contrast agent injection devices, force or a related parameter for table weight monitoring, and so forth. Where required, interface circuitry 130 is provided for conditioning signals received from the sensors 128 before application of the signals to processing circuitry 122. It should be noted that in addition to the exchange of data in the topology of FIG. 5, power may also be transmitted between the devices such as for powering processing circuit 122 and sensors 128.

Where desired, interface circuitry 126 may be provided in each device for encrypting and decrypting stored data. As will be appreciated by those skilled in the art, such circuitry will generally translate data stored and processed within the device to an encrypted or decrypted form so as to limit access or the utility of the data to external circuits. Interface 126 may further include circuitry for verification of the identity of a requesting circuit as described below. Such identification is particularly useful in limiting access of the stored data by external circuitry, devices, and personnel.

The topology provided in the embodiment of FIG. 5 may be based upon any suitable programming code and architecture. In a preferred embodiment, a product family available from Dallas Semiconductor of Dallas, Tex., under the commercial designation Crypto iButton, serves as the platform for the topology. Such devices were installed in a quick disconnect box for a variety of RF coils of an MRI system. The devices were then programmed to contain manufacturing and calibration data specific to each coil, as well as a dynamically updated record of the total number of uses of the coil. In operation, as each RF coil was coupled to a standard coil receptacle, the coil was automatically identified by the imaging system interface and the interface was updated to reflect insertion of the coil, including an electronic image of the coil itself, provided on a monitor (see monitor 48 in FIG. 1). The system was made back-compatible for coils not equipped with the preferred data topology by prompting the user to select a coil from a list of candidate coils when the coil was not identified during the initial connection sequence. The device included a single-chip trusted microcomputer as processing circuit 122, equipped with a Java virtual machine, a 1024-bit math accelerator, and an unalterable real time clock. Memory circuit 124 included a 6 Kbyte random access memory and a 32 Kbyte read-only memory. The processing functions included RSA encryption.

More limited topographies are, of course, available in the present technique. For example, where no processing capabilities are required, or very limited capabilities are required, specific analog or digital circuitry may be provided in the topology for this purpose. Moreover, memory-only devices may be provided in which data is merely stored and accessed.

Figure 6:
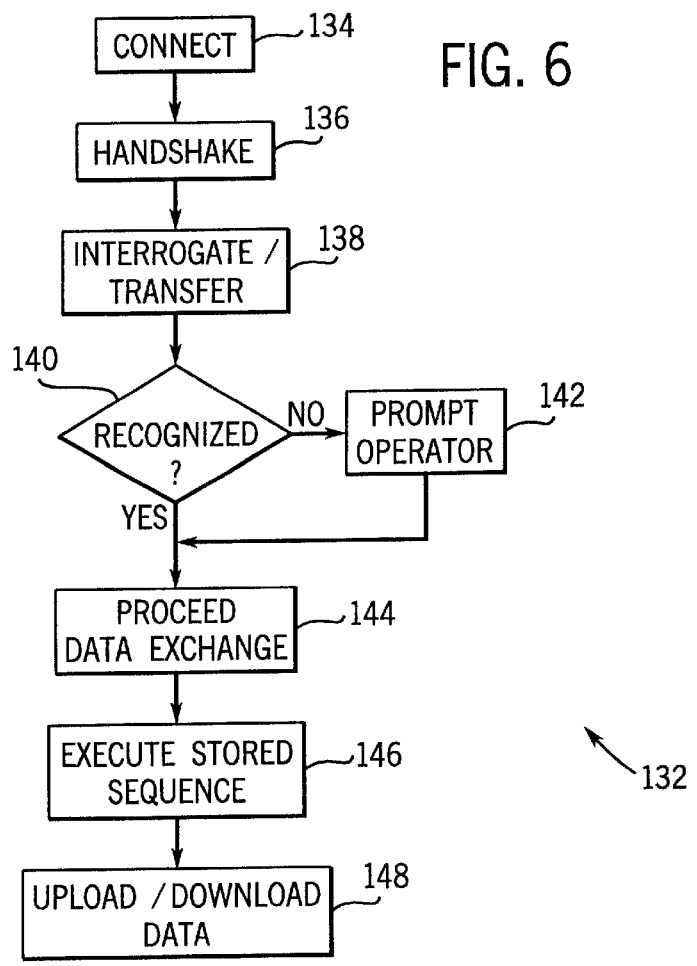
FIG. 6 is a flow chart illustrating exemplary control logic in storing and accessing data in accordance with aspects of the present technique.

FIG. 6 illustrates exemplary control logic, designated generally by reference numeral 132, for data management through a device equipped as illustrated in FIG. 5 in accordance with the present technique. As noted above, the device is first connected to other system components, as indicated at step 134. In practice, separable peripheral devices or subsystems may be physically connected at this step, or resident peripheral devices and subsystems may be connected during installation.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A medical diagnostic imaging system comprising:
an image data acquisition system for generating digital data representative of an image of a subject of interest;
a control system coupled to the image data acquisition system for regulating acquisition of the data; and
a peripheral device coupled to and controlled by the control system, the peripheral device including a memory circuit and an interface circuit, the memory circuit being configured to store parameter data descriptive of a characteristic of interest of the peripheral device, the interface circuit being configured to access the parameter data and to transmit the parameter data from the peripheral device upon demand.

2. The system of claim 1, wherein the peripheral device includes a digital data processing circuit coupled to the memory circuit and to the interface circuit for executing a predetermined processing routine on the parameter data.

3. The system of claim 2, wherein the peripheral device includes a sensor for generating a signal representative of the characteristic of interest, the processing circuit processing signals generated by the sensor and storing resulting parameter data in the memory circuit.

4. The system of claim 3, wherein the sensor is a load sensor.

5. The system of claim 3, wherein the sensor is an acoustic sensor.

6. The system of claim 3, wherein the sensor is a temperature sensor.

7. The system of claim 1, wherein the parameter data includes an identification of the peripheral device.

8. The system of claim 1, wherein the parameter data includes calibration data for the peripheral device.

9. The system of claim 1, wherein the parameter data includes data descriptive of a service history for the peripheral device.

10. The system of claim 1, wherein the imaging system is a magnetic resonance imaging system, and wherein the peripheral device is a radio frequency coil assembly.

11. The system of claim 1, wherein the peripheral device is a support for receiving a subject to be imaged.

12. The system of claim 1, wherein the peripheral device is a monitor for generating signal s representative of a physiological parameter of a subject to be imaged.

13. The system of claim 1, further comprising an operator interface system coupled to the control system, the operator interface system being configured to access the parameter data from the peripheral device upon demand.

14. The system of claim 1, wherein the peripheral device further includes a data encryption circuit for encrypting and decrypting data exchanged between the peripheral device and the control system.

15. A medical diagnostic imaging system comprising:
- an image data acquisition system for generating digital data representative of an image of a subject of interest;
- a control system coupled to the image data acquisition system for regulating acquisition of the data; and
- a peripheral device coupled to and controlled by the control system, the peripheral device including a data processing circuit, a memory circuit and an interface circuit, the memory circuit being configured to store parameter data descriptive of a characteristic of interest of the peripheral device, the data processing circuit being configured to process and store data, and the interface circuit being configured to access the parameter data and to transmit the parameter data from the peripheral device upon demand.

16. The system of claim 15, wherein the interface circuit is configured to receive data from an external source for storage in the memory circuit.

17. The system of claim 15, wherein the memory circuit is configured to store a desired executable routine for the processing circuit.

18. The system of claim 17, wherein the executable routine includes a calibration sequence for the peripheral device.

19. The system of claim 17, wherein the executable routine includes an initialization sequence for providing parameter data from the peripheral device to the control system following connection of the peripheral device to the control system.

20. The system of claim 19, wherein the processing circuit is configured to execute the initialization automatically without operator intervention.

21. The system of claim 15, wherein the peripheral device includes a sensor for generating a signal representative of the characteristic of interest, the processing circuit processing signals generated by the sensor and storing resulting parameter data in the memory circuit.

22. The system of claim 15, wherein the parameter data includes an identification of the peripheral device.

23. The system of claim 15, wherein the parameter data includes calibration data for the peripheral device.

24. The system of claim 15, wherein the parameter data includes data descriptive of a service history for the peripheral device.

25. The system of claim 15, wherein the imaging system is a magnetic resonance imaging system, and wherein the peripheral device is a radio frequency coil assembly.

26. The system of claim 15, wherein the peripheral device is a support for receiving a subject to be imaged.

27. The system of claim 15, wherein the peripheral device is a monitor for generating signals representative of a physiological parameter of a subject to be imaged.

28. The system of claim 15, further comprising an operator interface system coupled to the control system, the operator interface system being configured to access the parameter data from the peripheral device upon demand.

29. A magnetic resonance imaging system comprising:
- an image data acquisition system configured to generate digital image data for reconstruction into a diagnostic image, the image data acquisition system including a peripheral device having a memory circuit for storing parameter data representative of a parameter of the peripheral device and an interface circuit for accessing and transmitting the stored parameter data upon demand; and
- a control system coupled to the image data acquisition system, the control system being configured to access the parameter data from the peripheral device and to regulate acquisition of the digital image data at least partially based upon the parameter data.

30. The system of claim 29, wherein the parameter data includes an identification of the peripheral device.

31. The system of claim 29, wherein the parameter data includes calibration data for the peripheral device.

32. The system of claim 29, wherein the wherein the peripheral device includes a processing circuit for processing parameter data stored in the memory circuit.

33. The system of claim 29, wherein the interface circuit is configured to receive data from the control circuit and to store the received data in the memory circuit.

34. The system of claim 29, wherein the peripheral device is a radio frequency coil assembly.

35. A peripheral device for a medical diagnostic imaging system, the imaging system including an image data acquisition system and a control system for regulating acquisition of image data by the acquisition system, the peripheral device comprising:
- a memory circuit for storing parameter data descriptive of a characteristic of interest of the peripheral device; and
- an interface circuit coupled to the memory circuit and configured to be coupled to the control circuit of the imaging system to exchange the parameter data between the memory circuit and the control circuit.

36. The peripheral device of claim 35, further comprising a data processing circuit for processing the parameter data.

37. The peripheral device of claim 36, further comprising a sensor for generating a signal representative of a sensed parameter, the processing circuit processing signals from the sensor for storage in the memory circuit.

38. The peripheral device of claim 37, wherein the sensor is a load sensor.

39. The peripheral device of claim 37, wherein the sensor is a temperature sensor.

40. The peripheral device of claim 36, wherein the memory circuit is configured to store a n executable routine processed by the processing circuit.

41. The peripheral device of claim 40, wherein the executable routine includes a data exchange routine for providing the parameter data to the control circuit following connection of the peripheral device to the imaging system.

42. A method for managing peripheral data in an imaging system, the method comprising the steps of:
- providing a peripheral device including a memory circuit and an interface circuit, the memory circuit being configured to store data representative of a characteristic of interest of the peripheral device, the interface circuit being configured to access the stored data and to transmit the stored data to an external device;
- storing peripheral data in the memory circuit of the peripheral device, the peripheral data remaining resident in the peripheral device;
- connecting the peripheral device to a control system; and
- accessing the peripheral data from the memory circuit via the control system.

43. The method of claim 42, wherein the peripheral data is representative of manufacturing information for the peripheral device and is stored in the memory circuit following manufacture of the device.

44. The method of claim 42, wherein the peripheral data is representative of calibration information for the peripheral device and is stored in the memory circuit following a calibration sequence preformed on the peripheral device.

45. The method of claim 42, wherein the peripheral data is representative of service history activities for the peripheral device and is stored in the memory circuit following a service event.

46. The method of claim 42, wherein the peripheral data is representative of an identification of the peripheral device.

47. The method of claim 42, wherein the control system controls acquisition of image data in an imaging system, and wherein the peripheral data is accessed by the control system for use in performing an image data acquisition routine.

48. The method of claim 47, wherein the control system accesses the peripheral data from the memory circuit automatically during an initialization sequence following connection of the peripheral device to the imaging system.

* * * * *